(12) United States Patent
Pekonen et al.

(10) Patent No.: US 11,534,075 B2
(45) Date of Patent: Dec. 27, 2022

(54) HEART ACTIVITY MONITORING DURING PHYSICAL EXERCISE

(71) Applicant: Polar Electro Oy, Kempele (FI)

(72) Inventors: Elias Pekonen, Oulu (FI); Juhani Kemppainen, Oulu (FI)

( * ) Notice: Subject to any disclaimer, the term of this patent is extended or adjusted under 35 U.S.C. 154(b) by 1242 days.

(21) Appl. No.: 14/767,225

(22) PCT Filed: Feb. 14, 2013

(86) PCT No.: PCT/FI2013/050175
§ 371 (c)(1),
(2) Date: Aug. 11, 2015

(87) PCT Pub. No.: WO2014/125159
PCT Pub. Date: Aug. 21, 2014

(65) Prior Publication Data
US 2016/0000336 A1    Jan. 7, 2016

(51) Int. Cl.
| | | |
|---|---|---|
| *A61B 5/0245* | (2006.01) | |
| *A61B 5/00* | (2006.01) | |
| *A61B 5/08* | (2006.01) | |
| *A61B 5/349* | (2021.01) | |
| *A61B 5/352* | (2021.01) | |

(52) U.S. Cl.
CPC .......... *A61B 5/0245* (2013.01); *A61B 5/0816* (2013.01); *A61B 5/349* (2021.01); *A61B 5/352* (2021.01); *A61B 5/6823* (2013.01); *A61B 5/7203* (2013.01); *A61B 5/726* (2013.01)

(58) Field of Classification Search
CPC .............. A61B 5/04011; A61B 5/0452; A61B 2503/10; A61B 5/02405; A61B 5/04012
See application file for complete search history.

(56) References Cited

U.S. PATENT DOCUMENTS

| | | | | |
|---|---|---|---|---|
| 5,025,795 | A * | 6/1991 | Kunig | A61B 5/029 600/509 |
| 2005/0222513 | A1* | 10/2005 | Hadley | A61B 5/0452 600/515 |
| 2006/0235315 | A1* | 10/2006 | Akselrod | A61B 5/02405 600/509 |
| 2010/0137727 | A1* | 6/2010 | Sameni | A61B 5/0444 600/511 |
| 2011/0137191 | A1 | 6/2011 | Kinnunen | |
| 2012/0197148 | A1* | 8/2012 | Levitan | A61B 5/02405 600/515 |

(Continued)

OTHER PUBLICATIONS

F. Chiarugi, V. Sakkalis, D. Emmanouilidou, T. Krontiris, M. Varanini and I. Tollis, "Adaptive threshold QRS detector with best channel selection based on a noise rating system," 2007 Computers in Cardiology, 2007, pp. 157-160, (Year: 2007).*

(Continued)

*Primary Examiner* — Allen Porter
(74) *Attorney, Agent, or Firm* — FisherBroyles, LLP

(57) ABSTRACT

A method, apparatus, and computer program monitor a user's heart activity during a physical exercise. A heart activity measurement signal representing the user's heart activity is acquired and a phase component of the heart activity measurement signal is monitored. On the basis of the monitoring of the phase component, one or more actions are carried out.

12 Claims, 8 Drawing Sheets

(56) References Cited

U.S. PATENT DOCUMENTS

| | | | | |
|---|---|---|---|---|
| 2013/0116588 A1* | 5/2013 | Yazicioglu | ............. | A61B 5/726 600/521 |
| 2014/0031712 A1* | 1/2014 | Herskovitz | ............. | G16Z 99/00 600/545 |
| 2015/0241505 A1* | 8/2015 | Freeman | ............. | A61B 5/0402 324/538 |

OTHER PUBLICATIONS

Moody et al., "Derivation of Respiratory Signals from Multi-Lead ECGs", Proceedings of the Computers in Cardiology Meeting, IEEE Comp. Soc., Press, US, vol. Meeting 12, pp. 113-116 (Sep. 8, 1985).

International Search Report for corresponding PCT Application No. PCT/FI2013/050175, pp. 1-9, dated Oct. 10, 2013.

\* cited by examiner

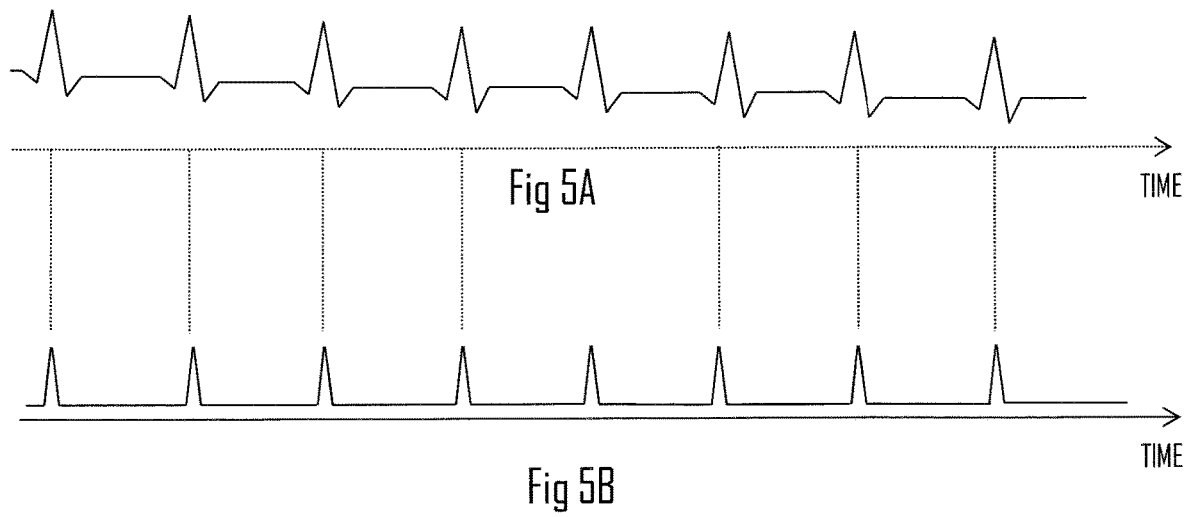
Fig 5A
Fig 5B
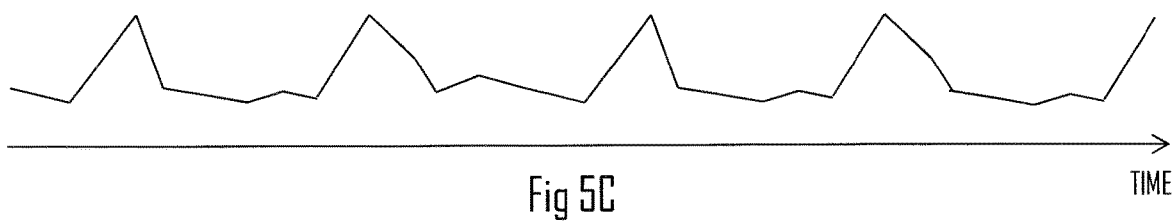
Fig 5C
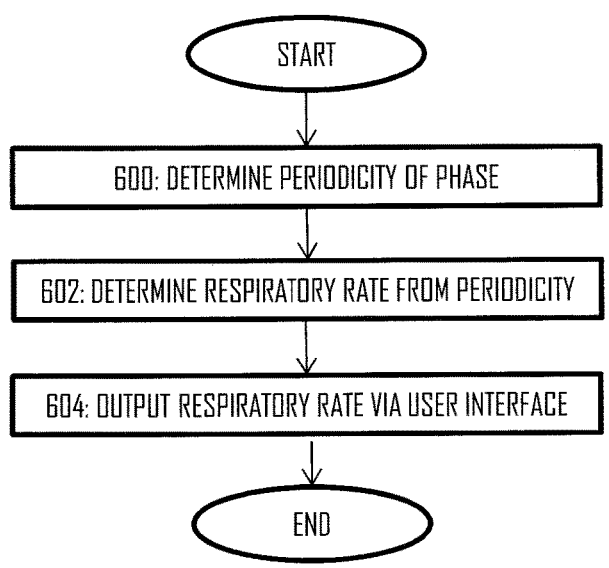
Fig 6

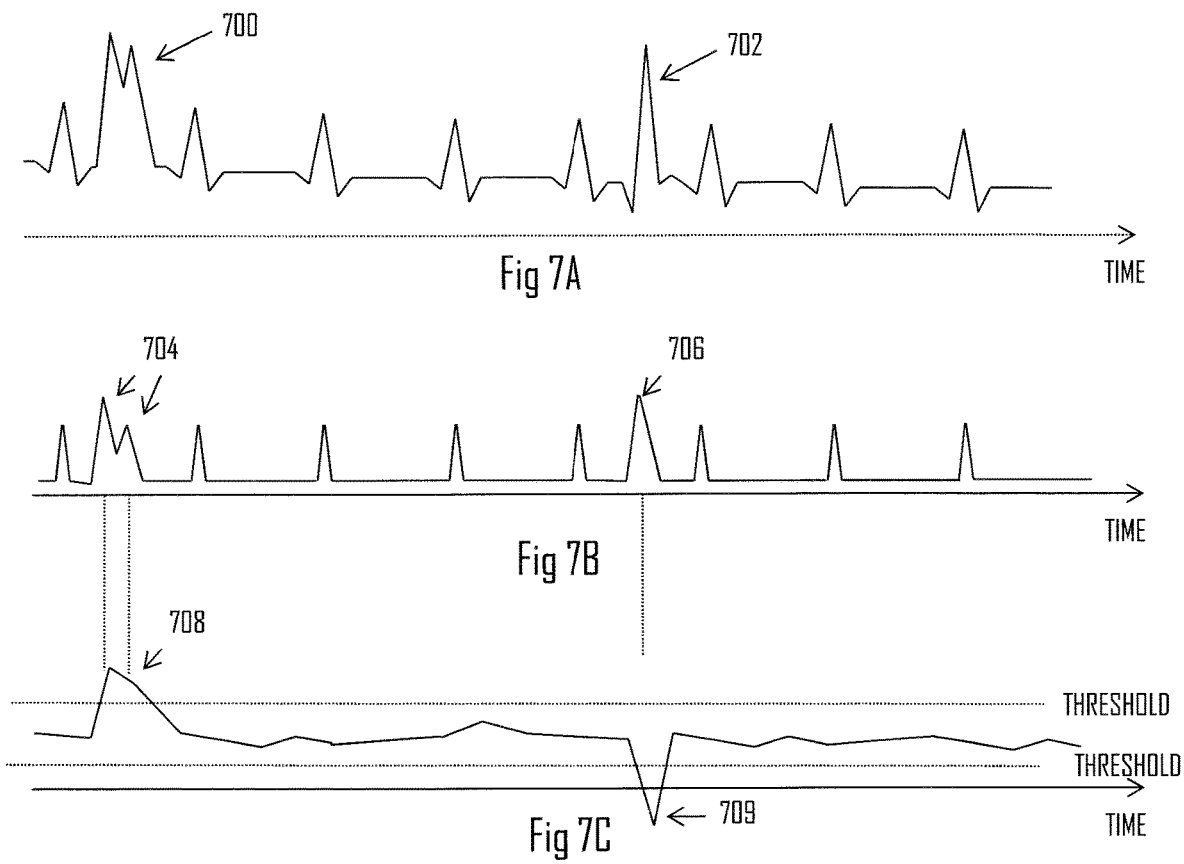
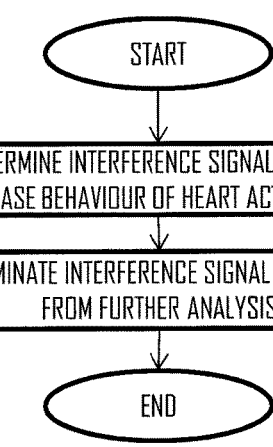
Fig 8

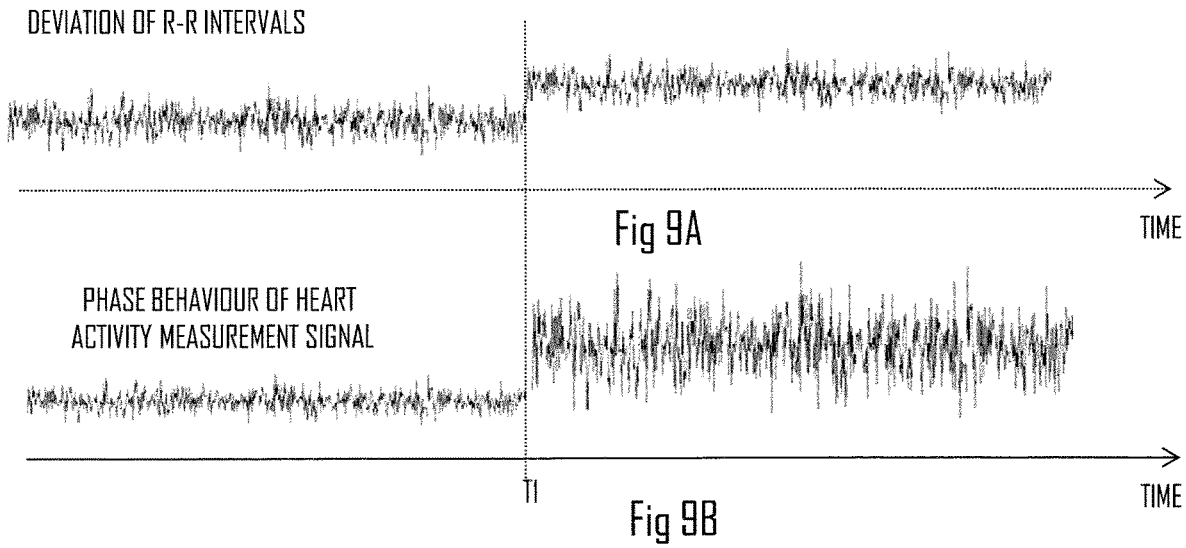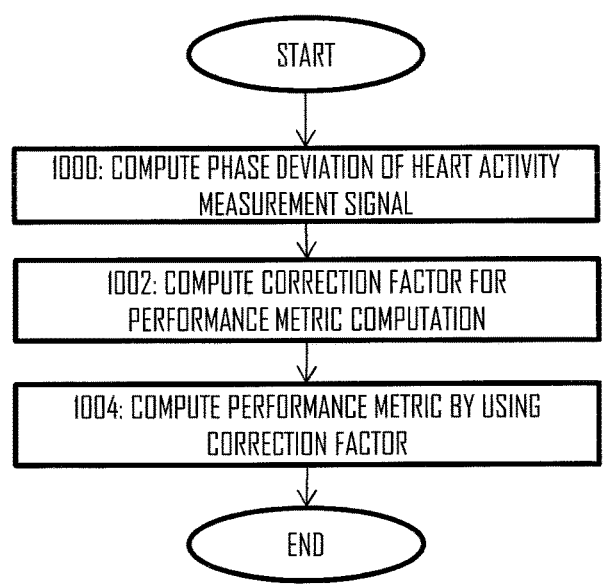

HEART ACTIVITY MONITORING DURING PHYSICAL EXERCISE

CROSS-REFERENCE TO RELATED APPLICATION

This application is a National Stage application of International Application No. PCT/FI2013/050175, filed Feb. 14, 2013, which is incorporated by reference herein in its entirety.

BACKGROUND

1. Field

The invention relates to the field of training devices and, particularly to training devices monitoring heart activity of a user during a physical exercise.

2. Description of the Related Art

Personal training devices monitoring heart activity of a user have been in commercial use. Such training devices typically comprise electrodes that are placed into contact with the user's skin, and they measure a heart activity signal such as an electrocardiogram (ECG) signal non-invasively from the user's skin by using electric sensors, for example.

SUMMARY

The invention is defined by the independent claims.
Embodiments of the invention are defined in the dependent claims.

BRIEF DESCRIPTION OF THE DRAWINGS

Embodiments of the present invention are described below, by way of example only, with reference to the accompanying drawings, in which

FIGS. 5A to 5C illustrate the heart activity measurement signal and its components;

FIG. 6 illustrates a flow diagram of a process for determining a physiological parameter from the phase component of the heart activity measurement signal according to an embodiment of the invention;

FIGS. 7A to 7C illustrate the heart activity measurement signal and its components with an interference signal component;

FIG. 8 illustrates a flow diagram of a process for detecting the interference signal components from the phase component of the heart activity measurement signal according to an embodiment of the invention;

FIGS. 9A and 9B illustrate correlation between deviation of R-R intervals and phase behaviour of the heart activity measurement signal;

FIG. 10 illustrates a flow diagram of a process for determining a correction factor for computation of a performance metric from the phase component of the heart activity measurement signal according to an embodiment of the invention;

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
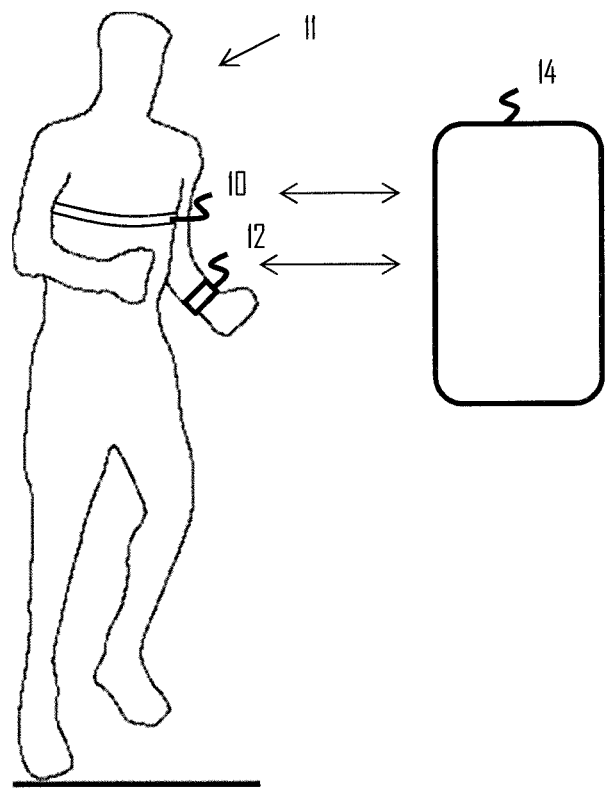
FIG. 1 illustrates an exercise monitoring system according to an embodiment of the invention.

FIG. 1 illustrates an embodiment of a personal training system comprising a sensor device 10 configured to measure heart activity signals from a user's 11 body. The sensor device 10 may comprise one or a plurality of skin electrodes coupled to the user's 11 skin. The sensor device 10 may be based on detection of an electrocardiogram (ECG) signal from the user's 11 skin. The heart activity measurement signals measured from the user's body may comprise the ECG signal being detected and, possibly, noise and interference components.

The sensor device 10 may further comprise a wireless communication circuitry configured to transmit measured heart activity measurement signals to another device, e.g. a user interface device 12, 14. The user interface device 12, 14 may be configured to process the received heart activity measurement signals and to illustrate training processed from the heart activity measurement signals to the user 11 via a display unit, for example.

In an embodiment, the user interface unit device a wrist device 12.

In an embodiment, the user interface device is a portable computer 14 such as a mobile phone or a tablet computer.

Embodiments of the invention relate to monitoring properties of the heart activity measurement signals measured from the user's 11 skin. The embodiments may be carried out in any one of the above-described devices 10, 12, 14 or in any other device acquiring the heart activity measurement signals. The devices 10, 12, 14 may collectively be referred to as exercise monitoring apparatuses.

Figure 2:
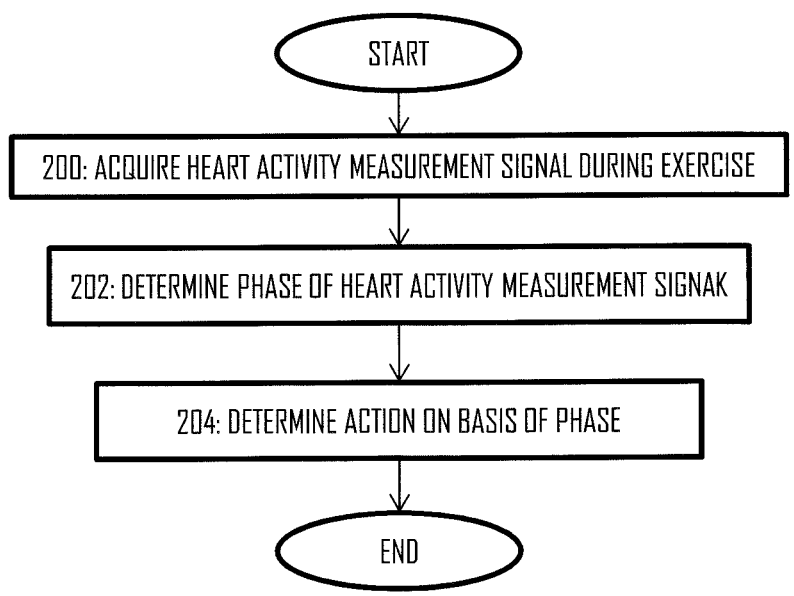
FIG. 2 illustrates a flow diagram of a process for monitoring the phase of a heart activity measurement signal measured from the user's body during a physical exercise.

FIG. 2 illustrates a method for processing a heart activity measurement signal in such an exercise monitoring apparatus. Referring to FIG. 2, the heart activity measurement signal of a user 11 is acquired during a physical exercise performed by the user in block 200. The heart activity measurement signal is measured by at least one electrode in contact with the user 11. In the embodiment where the method is carried out in the sensor device 10, the heart activity measurement signal may be acquired directly from said at least one electrode. In the embodiment where the method is carried out in the user interface device 12, 14, the heart activity measurement signal may be acquired wirelessly from the sensor device or from an internal sensor comprised in the user interface device 12, 14 and attached to the user 11.

In block 202, a phase of the heart activity measurement signal is monitored. A phase component of the heart activity measurement signal may be extracted from the received heart activity measurement signal as described below, for example. As described in this document, the phase of the heart activity measurement signal carries various information that may be used in improving the performance of the heart activity monitoring or even in determining other physiological parameters of the user 11. In block 204, an action to be performed is determined on the basis of the phase of the heart activity measurement signal, and said action is carried out.

In an embodiment, the action comprises is an output of an instruction to be provided to the user via a user interface.

In an embodiment, the action comprises eliminating interfering signal components from further processing of the heart activity measurement signal.

In an embodiment, the action comprises determining a physiological parameter of the user other than heart activity or heart rate.

In an embodiment, the action comprises correcting measurement inaccuracies in the heart activity monitoring.

In an embodiment, the action comprises selecting a measurement configuration.

Figure 3:
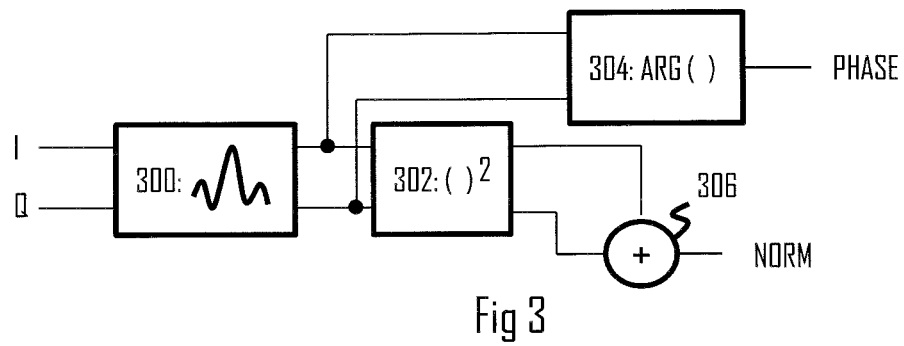
FIG. 3 illustrates a circuitry for extracting a phase component from the heart activity measurement signal according to an embodiment of the invention.

Before describing the various embodiments of using the phase of the heart activity measurement signal, let us consider an embodiment of extracting the phase from the acquired heart activity measurement signal with reference to FIG. 3. The acquired heart activity measurement signal may be processed into a complex form by generating an in-phase (I) component and a quadrature (Q) component of the heart activity measurement signal, wherein a phase shift is provided between the I component and the Q component, as known in the art of signal processing. The I and Q components of the heart activity measurement signal may then be processed with a wavelet transform 300. A wavelet used as a basis for the wavelet transform may be selected according to design requirements by taking into account processing capabilities, for example. In an embodiment, the wavelet is designed to have a bandwidth which is equal to or higher than a bandwidth of the heart activity measurement signal. The wavelet may be a Hanning wavelet, for example. In practical implementations, the wavelet transform may be approximated with a low pass filter designed according to the characteristics of the selected wavelet.

The phase of the heart activity measurement signal may be computed from the wavelet-transformed signal comprising the I and Q components by computing an argument of the signal (block 304). The computation of the argument may utilize arctangent function, as known in the art of signal processing. As an output of the argument computation in block 304, a phase component of the heart activity measurement signal is provided.

Similarly, amplitude or power characteristics of the heart activity measurement signal may be monitored by computing a second norm of the heart activity measurement signal. The second norm, also known as an Euclidean norm, may be computed by squaring the wavelet-transformed I and Q components of the heart activity measurement signal in block 302 and summing the squared I and Q components in block 306. The amplitude characteristics may be used in computation of a heart rate or R-R intervals of the heart activity measurement signal. An R-R interval refers to a time interval between consecutive R-wave components in the heart activity measurement signal.

Figure 4:
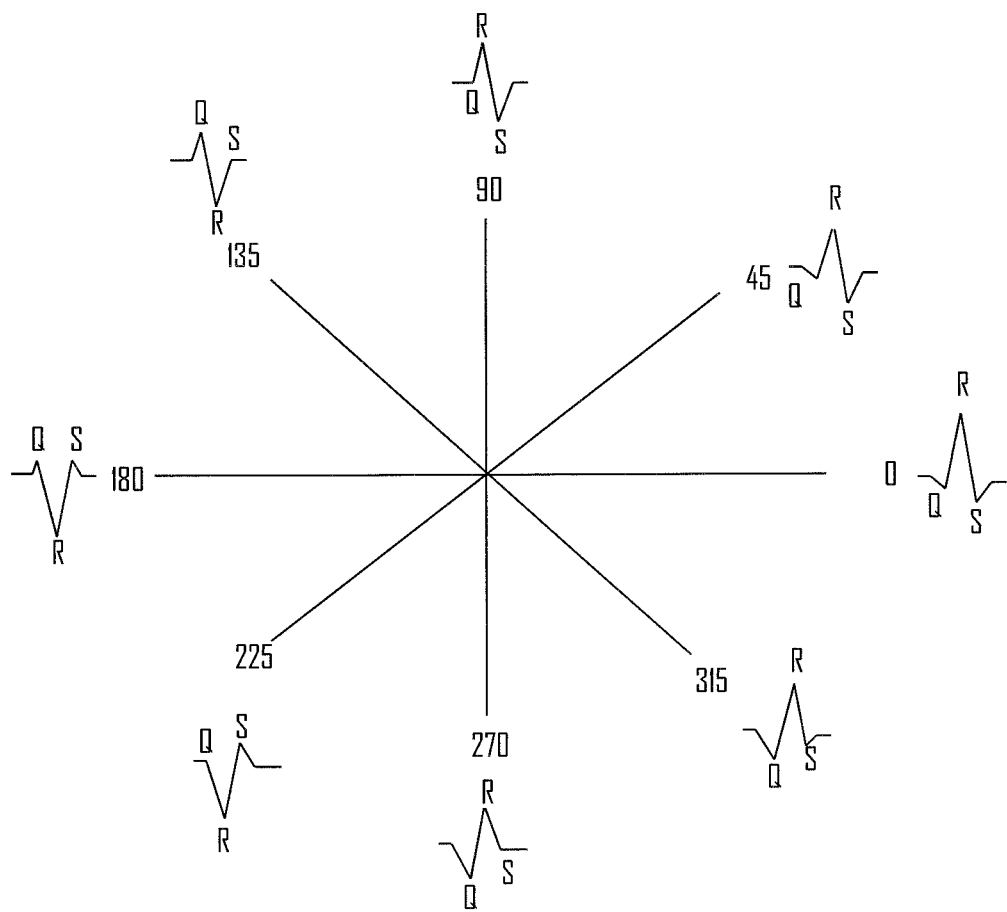
FIG. 4 illustrates a phase diagram and phases of a QRS complex waveform.

Let us now consider how the phase shift of the heart activity measurement signal affects a QRS complex waveform comprised in the heart activity measurement signal with reference to FIG. 4. FIG. 4 illustrates a phase diagram, wherein a QRS complex waveform has been illustrated in connection with phase shifts between 0 and 360 degrees. As can be seen in FIG. 4, phase shifts of 0 and 180 degrees result in an R wave having the highest amplitude. As the phase shifts from the 0 degrees towards 90 degrees, the amplitude of the R wave decreases and the amplitude of an S wave increases. Similarly, when the phase shifts from the 0 degrees towards 270 degrees, the amplitude of the R wave decreases and the amplitude of a Q wave increases. When closing the 180 degrees, the absolute value of the amplitude of the R wave again increases, and the QRS complex waveform with the phase shift of 180 degrees is a mirror image of the QRS complex waveform with the phase shift of 0 degrees. It can be deduced that a phase shift of 0 and 180 degrees provide the strongest R wave. Many heart activity detection procedures rely on detection of the R wave and, therefore, it is advantageous to provide a heart activity measurement signal having the strongest possible R wave in order to reduce the probability of not detecting the R wave or detecting the Q or S wave as the R wave. In this example, it would be beneficial to try to arrange the heart activity measurement signal to have a zero or 180 degree phase shift.

It should be appreciated that the phase diagram of FIG. 4 illustrates an example case, and in real implementations the optimal phase shift may be different, depending on the design of the signal processing. Referring to the embodiment of FIG. 3, the optimal phase shift(s) may be determined by the parameters of the wavelet transform or the phase shift properties of the (low-pass) filter. A person skilled in the art may easily find the analogy between the properties of the wavelet transform and, particularly, a phase shift of the wavelet used as a base for the transform, and the phase properties of the QRS complex waveform.

Let us now consider various embodiments for employing the phase component of the heart activity measurement signal with reference to FIGS. 5A to 15. First, let us consider with reference to FIGS. 5A to 6 an embodiment determining a physiological parameter of the user from the phase of the heart activity measurement signal. FIG. 5A illustrates the heart activity measurement signal in the form of a continuous ECG signal. In real implementations, the heart activity measurement may be sampled and analogue-to-digital (A/D) converted into a digital signal for signal processing. FIG. 5A illustrates the QRS complex waveforms used for determining a heart rate, for example. FIG. 5B illustrates a norm signal, e.g. the output of block 306. As shown in FIG. 5B, the norm signal shows clear and distinct peaks at the same timings with the QRS complex waveforms. The peaks may be used for computing R-R intervals and/or the heart rate, for example. A detection threshold may be used to detect the peaks.

FIG. 5C shows the phase component of the heart activity signal, e.g. the output of block 304. It can be seen that the phase component is a periodic signal. The dominating frequency component is directly proportional to a respiratory rate of the user. The respiratory rate is also known as a breathing frequency. The respiratory rate may be determined from the phase component of the heart activity signal by determining a dominating frequency component in the phase component. There are several state-of-the-art solutions for computing the dominating frequency component, e.g. by detecting peaks in the phase component and an inverse of an average time interval between the peaks or by computing a fast Fourier transform (FFT) of the phase component and detecting a frequency component containing the highest amount of energy.

Referring to FIG. 6, let us consider an embodiment of a process for determining the respiratory rate in the exercise monitoring apparatus. In block 600, the periodicity of the phase component of the heart activity measurement signal is determined by determining the dominating frequency component. In block 602, the respiratory rate is determined from the periodicity, wherein the respiratory rate may equal the periodicity. The respiratory rate may be stored in a memory unit of the exercise monitoring apparatus, it may be transmitted to another apparatus, and/or it may be output to the user 11 during the exercise (block 604). In the embodiment where the exercise monitoring apparatus is the sensor device 10 with no user interface, the sensor device 10 may transmit the respiratory rate to the user interface device 12, 14, and the user interface device 12, 14 may display or otherwise output the respiratory rate to the user 11 during the exercise. In the embodiment where the exercise monitoring apparatus is the user interface device 12, 14, the exercise monitoring apparatus may output the determined respiratory rate to the user via a user interface of the user interface device 12, 14 during the exercise. The respiratory rate may be illustrated to the user 11 via a display screen.

Next, let us describe an embodiment for using the phase component for eliminating interference components from the heart activity measurement signal and preventing them from affecting the analysis of the heart activity. FIG. 7A illustrates the heart activity measurement signal of FIG. 5A, wherein strong interference signal components 700, 702 have been summed into the ECG signal in the electrode(s), for example. Such strong interference may comprise motion artefacts resulting from the motion during the exercise (e.g. running), static electric components generated by the user 11 adjusting his/her shirt, etc. The interference signal components 700, 702 also show in the norm signal (FIG. 7B) as additional peaks 704, 706 that degrade the analysis of the heart activity. It may provide false readings for the heart rate, for example. It may be difficult to detect the interference signal components from the norm signal, because they show as very similar peaks than the peaks caused by the ECG signal that is being detected. Extraction of the interference signal components from the heart activity measurement signal (FIG. 7A) may be even more difficult, because the interference signals are typically more mixed with the ECG signal and noise.

FIG. 7C illustrates the phase behaviour of the heart activity measurement signal comprising the interference signal components 700, 702. As can be seen from FIG. 7C, the interference signal components 700, 702 create distinct peaks 708, 709 (a phase shift) to the phase component. The phase of the ECG signal remains substantially constant over time (it has the periodic feature illustrated in FIG. 5C), but the phase shifts caused by the interference signal components are typically strong and random in nature. The phase variation caused by the interference signal components may be stronger or much stronger than the phase variation caused by the respiratory rate. These interference peaks 708, 709 in the phase component may be detected and signal components having the timing of the detected peaks of the phase component may be eliminated from the heart activity measurement signal (FIG. 7A) and/or from the norm signal (FIG. 7B) such that they will not affect further analysis of the signal(s).

Let us now consider an embodiment for eliminating or reducing interference signal components with reference to FIG. 8. In block 800, the interference signal components 700, 702 in the heart activity measurement signal (FIG. 7A) are detected from the phase behaviour of the heart activity measurement signal (FIG. 7C). Block 800 may comprise determining an average level of the phase of the heart activity measurement signal, determining a timing of phase samples of the heart activity measurement signal that deviate from the average level, and eliminating signal components of the heart activity measurement signal and/or the norm signal having said determined timing from further analysis (block 802). For example, a signal detection circuitry detecting the QRS complex waveforms from the norm signal may be configured to disregard signal components having the timing of the phase offsets 708, 709 caused by the interference signal components 700, 702. If the detection of the QRS complex waveforms is based on peak detection, the signal detection circuitry may eliminate or disregards any peaks having the timing of the determined interference signal components, e.g. it may eliminate the peaks 704, 706.

In the detection of the timing of the interference signal components from the phase component of FIG. 7C, the average level of the phase component may first be determined. As described above, the phase of the ECG signal remains substantially constant, and the average level may be used to approximate the phase of the ECG signal. The average level may be computed by computing a mean or a median of the phase component within a determined sampling window. Therefore, the concept of average level represents an effective value of a plurality of successive phase values. As shown in FIG. 7C, a tolerance zone may be provided around the average level. The tolerance zone may be defined by a range or by an upper and a lower threshold. Any phase component falling outside the tolerance zone may be determined to be caused by an interference signal component, and the timing of such phase component samples may be stored for the elimination of the corresponding interference signal components in block 802. The tolerance zone may be provided around the average level, because interference signal components typically cause a phase shift that may be a positive or negative offset (see phase shifts 708, 709 in FIG. 7C).

Let us next describe an embodiment where the phase component is used to improve accuracy of estimation of a performance metric. In particular, the phase component may be used to derive a correction factor that may be used to correct estimation inaccuracies in the performance metric. In an embodiment, the performance metric is computed from a heart rate variability derived from the heart activity measurement signal.

In an embodiment, the performance metric characterizes user's physiological state before, during, or after training.

In an embodiment, the performance metric characterizes an exertion level of the user.

In an embodiment, the performance metric characterizes the status of the user's sympathetic and/or parasympathetic nervous system before, during or after training.

In an embodiment, the performance metric characterizes the fitness level of the user.

In an embodiment, the performance metric characterizes user's estimated time to recover from the training.

In an embodiment, the performance metric characterizes the stress level of the user.

A signal shown in FIG. 9A illustrates a deviation of R-R intervals of the heart activity measurement signal over time. As can be seen, an average level of the deviation rises at time instant T1 to a next level and stays there. This kind of behaviour may result from a change in the measurement configuration (e.g. a positioning of the electrodes) or in environmental conditions affecting the measurement of the ECG signal. FIG. 9B illustrates the phase component of the heart activity measurement signal and it has been discovered that the deviation in the phase component increases in proportion to the increase in the deviation of the R-R intervals. Additionally, FIG. 9B shows a shift in the average level of the phase component, and the shift may be caused from the change in the measurement configuration, for example. However, this embodiment utilizes the increase in the deviation (or variance or variability) of the phase component. Let us describe a process for using the phase component to improve the accuracy of the performance metric with reference to FIG. 10. In block 1000, a deviation of the phase component of the heart activity measurement signal is computed. The phase deviation may be a standard deviation of the phase within a determined observation window. In block 1002, a correction factor is computed from the phase deviation. In block 1004, the correction factor is used in computation of the performance metric based on the heart rate variability. Correlation between the deviation of the phase component and the deviation of the R-R intervals is found to be linear or at least approximately linear.

In an embodiment where the deviation of the R-R intervals is monitored, the correction factor scales and/or offsets the computed deviation of the R-R intervals, e.g. the computed deviation of the R-R intervals may be divided by the computed deviation of the phase component. In another embodiment, the computed deviation of the R-R intervals is multiplied by factor "a" and offset by a factor "b" as:

$$D_{R-R\_Corrected} = aD_{R-R} + b \quad (1)$$

where $D_{R-R}$ represents the computed deviation of the R-R intervals, and $D_{R-R\_Corrected}$ represents the deviation of the R-R intervals after the correction. Factor "a" may be an inverse of the computed deviation of the phase component.

In an embodiment, an observation interval used for estimating the performance metric is adjusted on the basis of the deviation of the phase component. High deviation of the phase may increase errors in the detection of the QRS complexes (see description of FIG. 4), and the observation interval may be adjusted such that a longer observation (or averaging) interval may be used for higher deviation of the phase component, and a shorter observation interval may be used for a lower deviation of the phase component. By using a longer observation interval for averaging, an effect of erroneous or missing detections of the QRS complexes on the performance metric reduces.

Figure 11:
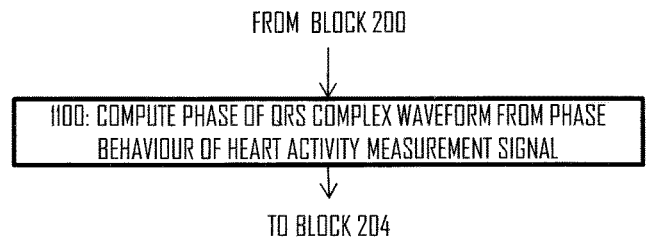
FIG. 11 illustrates a flow diagram of a process for computing a phase of a QRS complex waveform from the phase component of the heart activity measurement signal according to an embodiment of the invention.
Figure 12:
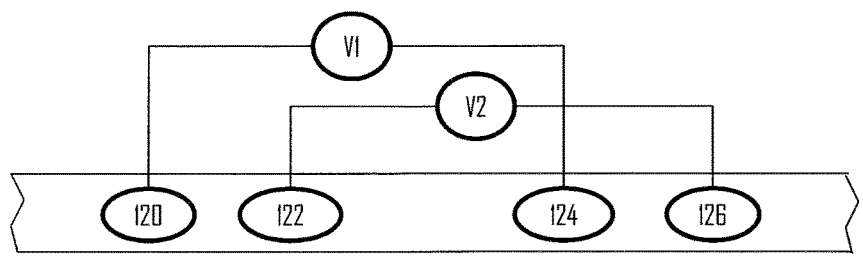
FIG. 12 illustrates an embodiment of a measurement configuration for measuring the heart activity of the user.
Figure 13:
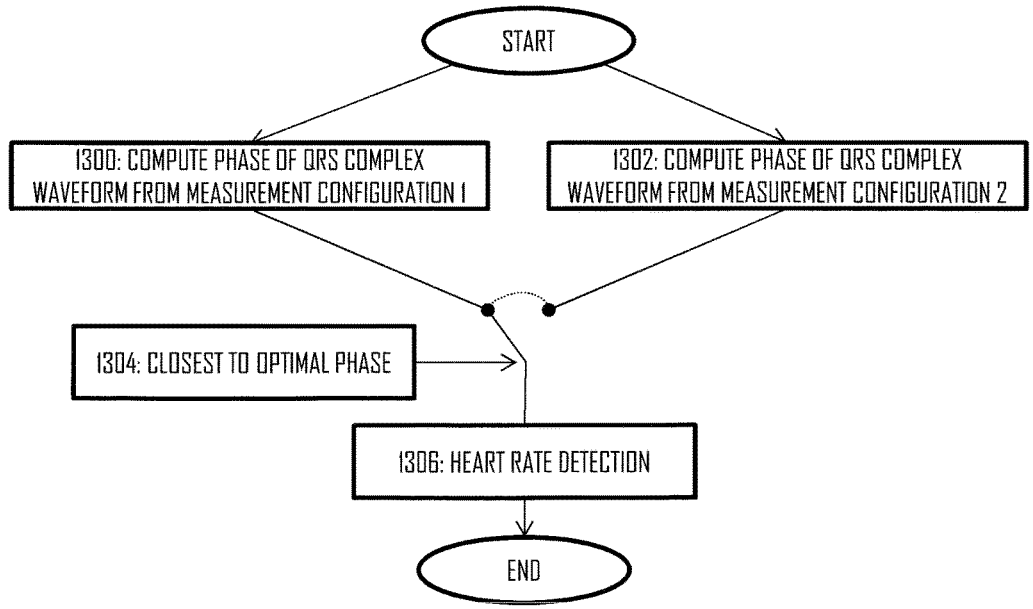
FIG. 13 illustrates a flow diagram of a process for determining an optimal measurement configuration from the phase component of the heart activity measurement signal according to an embodiment of the invention.
Figure 14:
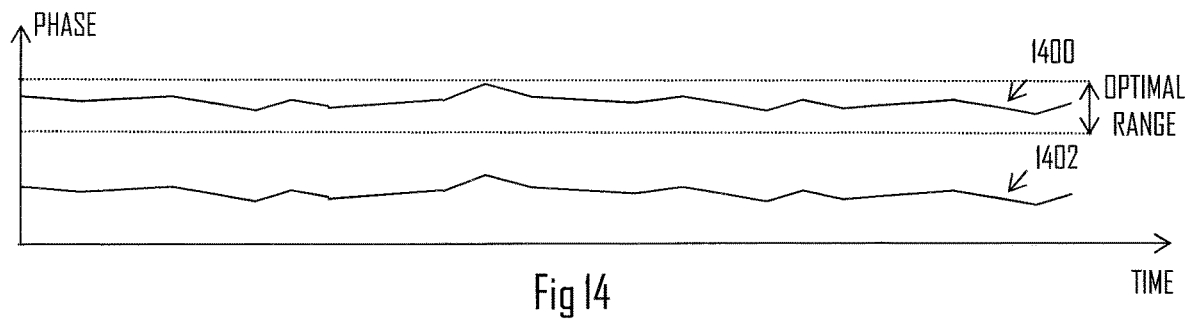
FIG. 14 illustrates phase behaviour of heart activity measurement signals.

As described above in connection with FIG. 4, the phase of the QRS complex may affect the performance of any analysis of the heart rate measurement signal that utilizes the detection of the QRS complex waveform. Therefore, it may be advantageous to try to detect the phase of the QRS complex waveform and try to arrange it to be optimal for the detection of the QRS complex waveform. FIG. 11 illustrates an embodiment of block 202, wherein a phase of the QRS complex waveform is detected from the phase component of the heart activity measurement signal in block 1100. In an embodiment, the phase of the QRS complex waveform is computed from the average level of the phase component. The computation of the average level of the phase component may be carried out when computing the average level for the interference component elimination, as described above, or it may be carried out after the interference signal components have been identified and eliminated from the phase component as well. In the latter embodiment, accuracy of the estimation of the phase of the QRS complex waveform may be improved. FIGS. 12 to 14 illustrate embodiments for adjusting the phase of the QRS complex waveform.

As a background for the embodiments of FIGS. 13 and 14, it is known that vectors of an ECG signal of different users may have different directions which may affect the measurement of the ECG signal. A given positioning of the electrode(s) may be optimal for one user but sub-optimal for another user because of different directions of their personal ECG vectors. As a consequence, the positioning of the electrodes may have an effect on the phase of the QRS complex waveform (see FIG. 4), and wrong positioning may cause errors in detection of the QRS complex waveforms.

FIG. 12 illustrates an embodiment of a measurement configuration used for measuring the ECG signals from the user's body, e.g. from the skin surface. FIG. 12 illustrates a strap comprising a plurality of electrodes 120, 122, 124, 126. The number of electrodes may be at least three but, in general, the number of electrodes may be selected such that at least two different electrode subsets can be arranged to measure the ECG signal. In this example, electrodes 120, 124 are used to provide a first measurement configuration, and electrodes 122, 126 are used to realize a second measurement configuration. Due to the different positioning of the electrodes, each configuration is tuned to measure an ECG signal vector having a certain direction different from that to the vector direction(s) to which the other configuration(s) is/are tuned.

FIG. 13 illustrates a process for determining an optimal measurement configuration by detecting the phase of the QRS complex waveforms acquired with different measurement configurations and by selecting the measurement configuration providing the most optimal phase of the QRS complex waveform. Referring to FIG. 13, the phase of the QRS complex waveform is computed from a heart activity measurement signal provided by the first measurement configuration in block 1300. In block 1302, the phase of the QRS complex waveform is computed from a heart activity measurement signal provided by the second measurement configuration. Similarly, the phase of the QRS complex waveform is computed from one or more heart activity measurement signals provided by one or more other measurement configurations may be computed. The sensor device comprising the electrodes 120 to 126 may comprise a switching mechanism to select the electrodes to be used and, thus, switch between the different measurement configurations. In this manner, the different measurement configurations may employ partially the same components in the measurement. Only the set of electrodes may change. In block 1304, a measurement configuration providing the most optimal phase of the QRS complex is selected for use, and the heart rate detection and other analysis of the heart activity measurement signal (block 1306) is carried out by using the selected measurement configuration. The measurement configuration selection procedure of FIG. 13 may be repeated at determined intervals and/or upon detecting an event in the phase of the QRS complex waveform. For example, if the phase of the QRS complex waveform is detected to have shifted, the process of FIG. 13 may be repeated. The process of FIG. 13 may thus be used to correct the phase shift illustrated in connection with the embodiment of FIGS. 9A and 9B.

In some scenarios, the user 11 could improve the performance of the heart activity measurements by adjusting the electrode(s). For example, the electrodes may need moisture in order to ensure a sufficient electric coupling between the electrodes and the user's 11 skin and, at the beginning of the exercise, the user might improve the electric coupling by moistening the electrodes. According to another aspect referring to the direction of the ECG signal vector that may be unique to user, adjusting the positioning of the electrodes with respect to the user's 11 body might improve the quality of the QRS complex waveform and performance of the detection of the QRS complex.

Figure 15:
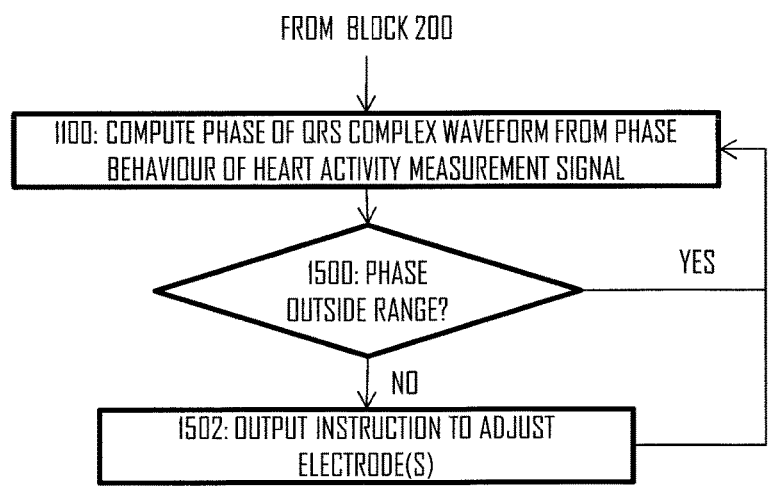
FIG. 15 illustrates a flow diagram of a process for instructing the user to adjust the measurement configuration on the basis of analysing the phase component of the heart activity measurement signal according to an embodiment of the invention.
Figure 16:
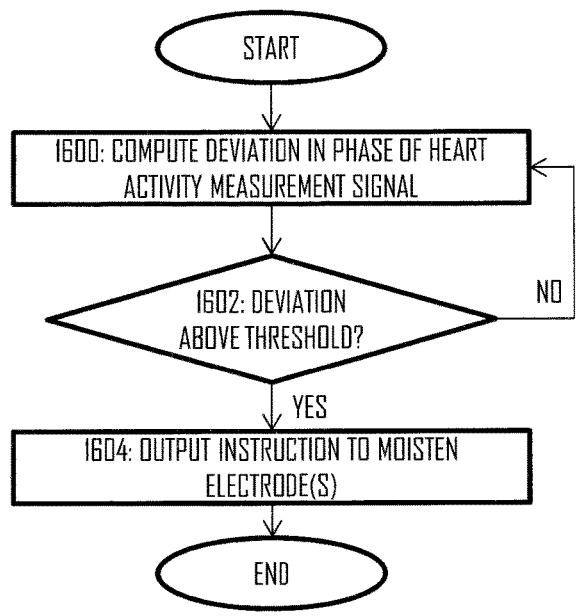
FIG. 16 illustrates a flow diagram of a process for monitoring deviation of the phase component of the heart activity measurement signal and instructing the user accordingly according to an embodiment of the invention.

In an embodiment, the exercise monitoring apparatus outputs, on the basis of analysing the phase component of the heart activity measurement signal, an instruction for the user to adjust at least one electrode measuring the heart activity data. FIGS. 14 to 16 illustrate embodiments for determining what type of adjustment of the electrodes is needed, and the instruction is selected accordingly. FIG. 14 illustrates two exemplary phase components of heart activity measurement signals. As described above in connection with FIGS. 12 and 13, the average level of the phase component represents the phase of the QRS complex waveform in the detection circuitry. Keeping the average level of the phase component within a determined range around at least one of the optimal phases of the QRS complex waveform causes efficient performance in the QRS complex detection. The determined range is called "optimal range" in FIG. 14. The phase component 1400 stays within the optimal range, so no adjustment is needed. However, the phase component 1402 is not within the optimal range, and the exercise monitoring apparatus detecting that the phase component 1402 is not within the optimal range may output the instruction for the user to change the positioning of the electrodes in order to change the direction of the ECG signal vector and change the phase of the QRS complex waveform. FIG. 15 illustrates a flow diagram of this process according to an embodiment of the invention. FIG. 15 illustrates an embodiment of blocks 202 and 204.

Referring to FIG. 15, the exercise monitoring apparatus computes the phase of the QRS complex waveform from the phase behaviour of the heart activity measurement signal in block 1100, as described in connection with FIG. 11. The phase of the QRS complex waveform may be computed by determining the average level of the phase component within an observation interval. Then, the phase of the QRS complex wave form may be compared with the optimal range determined by at least one phase threshold. In block 1500 it is determined whether or not the phase of the QRS complex waveform falls within the optimal range. If the phase of the QRS complex waveform is within the optimal range, the monitoring of the phase behaviour is continued and the process may return to block 1100. On the other hand, if the phase of the QRS complex waveform is outside the optimal range, the process proceeds to block 1502 in which the instruction to adjust the positioning of the electrodes is output to the user via the user interface. Typically, a lateral repositioning may cause a sufficient shift in the phase of the QRS complex waveform, so the output instruction may specify that the user is instructed to move the electrodes laterally with respect to the user's body, e.g. to the left or to the right. Thereafter, the monitoring of the phase of the QRS complex waveform may be continued in block 1100.

Motion artefacts caused by the user's 11 motion during the exercise may interfere with the measurements. A typical interference model is caused by the motion in connection with running, wherein the signal detection circuitry attempting to detect the QRS complexes ends up detecting motion artefacts caused by stride impacts, and the heart rate measurement is distorted to show stride rate. The impact in connection with each stride may cause motion of the electrodes with respect to the user's body or motion of clothes the user is wearing, and the result may be a high-level electric interference component induced to the electrodes. The appearance of the motion artefacts depends on the user; some users are prone to create the motion artefacts, particularly at the beginning of the exercise when the contact between the electrodes and the user's skin has not been improved by the natural moisture created by the human bod during the exercise. FIG. 16 illustrates an embodiment of a process for detecting the motion artefacts and instructing the user to adjust the electrodes to reduce the motion artefacts. Referring to FIG. 16, the exercise monitoring apparatus computes the deviation in the phase component of the heart activity measurement signal in block 1600. In an embodiment, the phase deviation is computed as:

$$Pd(n)=FIR*\mathrm{abs}(PP(n)) \qquad (2)$$

where FIR represents a low-pass filter, "*" represents a convolution operation, abs represents absolute value, and PP represent a difference between consecutive phase samples ($P(n)-P(n-1)$). The low-pass filter serves as an averaging function.

Since the motion artefacts are typically strong signal components and have random phase, they dominate over the ECG signal and increase the phase deviation of the phase component. Let us remind that the average level of the phase component stays relatively constant. In block 1602, it is determined whether or not the deviation is above a threshold. The threshold may be selected sufficiently high such that the deviation caused by the periodicity of the phase component described in connection with FIG. 5C does not cause the threshold being exceeded. Equally, any other metric proportional to the deviation may be used, e.g. the variance. If the deviation is below the threshold (or within an allowed range), the monitoring of the phase deviation is continued in block 1600. On the other hand, if the phase deviation is above the threshold (or outside the allowed range), the process proceeds to block 1604 in which an instruction is output to instruct the user to moisten the electrode(s). Moistening improves the electric contact and reduces the motion artefacts. This instruction may also be output via the user interface of the exercise monitoring apparatus or through a user interface of another apparatus, e.g. through the user interface device 12, 14 when the exercise monitoring apparatus is the sensor device 10.

Figure 17:
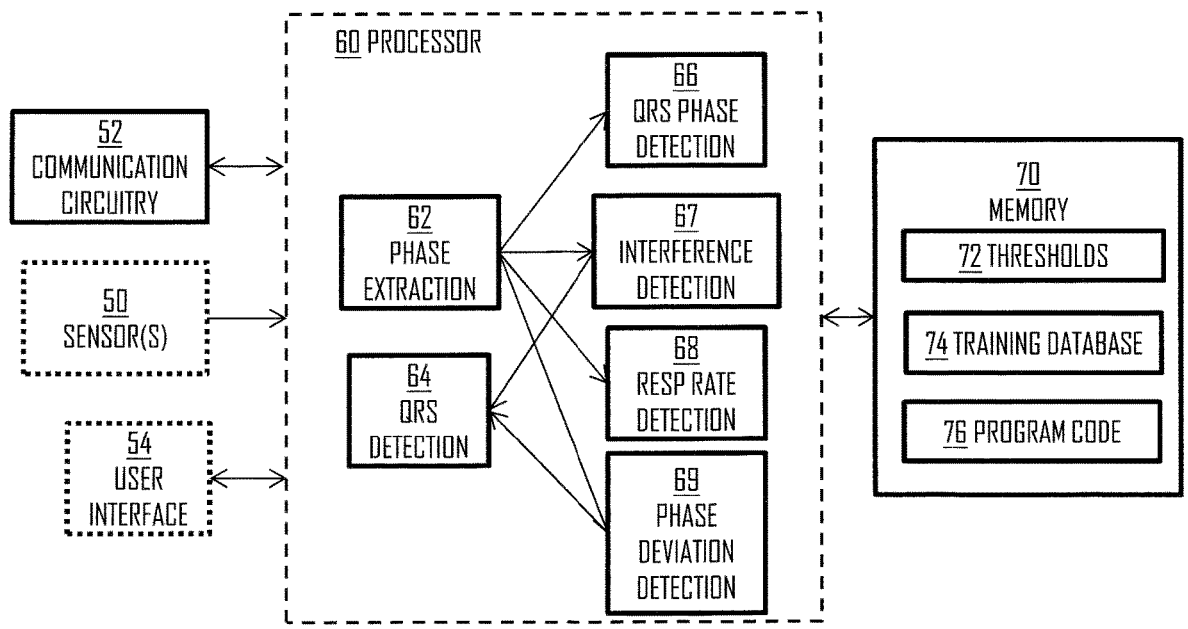
FIG. 17 illustrates a block diagram of an exercise monitoring apparatus according to an embodiment of the invention.

FIG. 17 illustrates a block diagram of the exercise monitoring apparatus according to an embodiment of the invention. As described above, the exercise monitoring apparatus may be sensor device 10, the user interface device 12, 14, or any other apparatus configured to monitor the heart activity measurement signals measured from the user's body during the physical exercise. The apparatus comprises a least one processor 60 and at least one memory 70 storing a computer program code 76. The computer program code 76 configures the processor to carry out embodiments of the invention, e.g. any one of the embodiments described above. The memory 70 may further store a training database 74 in which any parameters and performance metrics measured and/or computed during the exercise may be stored. The memory 70 may further store any thresholds 72 and/or any other parameters or criteria used in the embodiments described above.

The apparatus may further comprise a communication circuitry 52 providing the apparatus with communication capability. The communication circuitry may support any wired or wireless communication technique, e.g. Bluetooth, Bluetooth Low energy, IEEE 802.15, IEEE 802.11, W.I.N.D, ANT by Dynastream, or any other radio or induction-based communication technique. Depending on the embodiment, the apparatus may further comprise at least one sensor 50 configured to measure the heart activity of the user 11. The sensor(s) may comprise the above-described electrodes and appropriate circuitry to process the heart activity measurement signals. Depending on the embodiment, the apparatus may further comprise the user interface 54 for user interaction. The user interface 54 may comprise an output device and an input device. The output device may comprise a display unit (e.g. a liquid crystal display) and the input device may comprise one or more buttons or keys or a touch-sensitive display.

The processor 60 may comprise one or more sub-circuitries 62 to 69 configured to carry out the embodiments of the invention. The sub-circuitries 62 to 69 may be physical circuitries in the processor 60, or they may be realized by separate computer program modules, and the at least partially the same physical circuitries of the processor may carry out the operations of different modules 62 to 69.

The processor 60 may receive the heart activity measurement signal from the at least one sensor 50 or through the communication circuitry 52. The processor may comprise a phase extraction circuitry 62 configured to extract the phase component from the heart activity measurement signal and output the extracted phase component for further analysis. The processor 60 may further comprise a QRS detection circuitry 64 configured to detect the QRS complex waveform from the heart activity measurement signal. The operation of the QRS detection circuitry 64 may be based on detecting the R wave, for example. The QRS detection circuitry 64 or the processor 60 may then compute various performance metrics from the detected QRS waveforms, e.g. the heart rate, heart rate variability, energy consumption, and/or exertion level.

The processor 60 may comprise a QRS phase detection circuitry 66 configured to monitor the phase of the QRS complex waveform from the phase component received from the phase extraction circuitry 62, as described above in connection with FIGS. 11 to 15. The QRS phase detection circuitry 66 may be configured to carry out at least some of the actions on the basis of the detected phase of the QRS complex waveform, as described above. For example, the QRS phase detection circuitry may select an optimal measurement configuration (an optimal set of electrodes to provide the heart activity measurement signal) or control the user interface 54 to output an instruction for the user to adjust the positioning of the electrodes, e.g. to adjust the strap comprising the electrodes.

The processor 60 may comprise an interference detection circuitry 67 configured to determine the presence of the interference signal components in the heart activity measurement signal and control the elimination of the interference signal components from the analysis of the heart activity measurement signal. The interference detection circuitry may carry out the process described above in connection with FIGS. 7A to 8, and the interference detection circuitry may output the detected timings of the interference signal components to the QRS detection circuitry 64 such that the QRS detection circuitry 64 may eliminate any signal components having the timing received from the interference detection circuitry 67. In another embodiment, the interference detection circuitry may receive the heart activity measurement signal before it is input to the QRS detection circuitry 64, remove the interference signal components from the heart activity measurement signal, and output the interference-suppressed heart activity measurement signal to the QRS detection circuitry 64.

The processor 60 may further comprise a respiratory rate detection circuitry 68 configured to determine the user's respiratory rate from the periodicity of the phase component, as described above in connection with FIGS. 5 and 6.

The processor may further comprise a phase deviation detection circuitry 69 configured to monitor the phase deviation of the phase component. The phase deviation detection circuitry may carry out any one of the embodiments described above in connection with FIGS. 9A, 9B, 10, and 16, and carry out a corresponding action. For example, the phase deviation detection circuitry 69 may compute the correction factor for use in computation of the performance metric or the heart rate variability in the QRS detection circuitry 64, or the phase deviation detection circuitry 69 may output an instruction for the user to moisten the electrodes.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in FIGS. 4 to 8 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to exercise monitoring systems described above but also to other suitable exercise monitoring systems. The technology may evolve over time and the development may require extra changes to the described embodiments. Therefore, all words and expressions should be interpreted broadly and they are intended to illustrate, not to restrict, the embodiments. It will be obvious to a person skilled in the art that, as technology advances, the inventive concept can be implemented in various ways. The invention and its embodiments are not limited to the examples described above but may vary within the scope of the claims.

The invention claimed is:

1. An apparatus, the apparatus comprising:
at least one processor; and
at least one memory including a computer program code, wherein the at least one memory and the computer program code are configured, with the at least one processor, to cause the apparatus to perform operations comprising:
acquiring a heart activity measurement signal of a user during a physical exercise performed by the user, wherein the heart activity measurement signal comprises QRS complex waveforms and characterizes electric activity of the user's heart and is measured by at least one electrode pair in contact with the user's skin;
monitoring a phase component of the heart activity measurement signal by computing an argument of wavelet-transformed in-phase (I) and quadrature (Q) components of the heart activity measurement signal;
computing at least one of a deviation, variance and variability of the phase of the QRS complex waveforms within a determined window;
detecting that at least one of the deviation, variance and variability exceeds a predetermined threshold; and
outputting, in response to said detecting, an instruction for the user to adjust at least one electrode of the at least one electrode pair.

2. The apparatus of claim 1, wherein the at least one memory and the computer program code are configured, with the at least one processor, to cause the apparatus to perform operations comprising determining a physiological parameter of the user from the phases of the QRS complex waveforms of the heart activity measurement signal.

3. The apparatus of claim 2, wherein the at least one memory and the computer program code are configured, with the at least one processor, to cause the apparatus to perform operations comprising:
determining a periodicity of the phase component of the heart activity measurement signal within the determined window; and
determining a respiratory rate of the user from the periodicity of the phase component of the heart activity measurement signal within the determined window.

4. The apparatus of claim 1, wherein the at least one memory and the computer program code are configured, with the at least one processor, to cause the apparatus to perform operations comprising:
determining interference signal components in the acquired heart activity measurement signal on the basis of the phases of the QRS complex waveforms of the heart activity measurement signal; and
eliminating the determined interference signal components from further analysis of the heart activity measurement signal.

5. The apparatus of claim 4, wherein the at least one memory and the computer program code are configured, with the at least one processor, to cause the apparatus to perform operations comprising:
determining the phases of the QRS complex waveforms of the heart activity measurement signal;
determining a timing of phase samples of the heart activity measurement signal that deviate from the phases of the QRS complex waveforms more than a predefined threshold; and
eliminating signal components having said determined timing from further analysis of the heart activity measurement signal.

6. A method for processing a heart activity measurement signal in an exercise monitoring apparatus, the method comprising:
acquiring the heart activity measurement signal of a user during a physical exercise performed by the user, wherein the heart activity measurement signal comprises QRS complex waveforms and characterizes electric activity of the user's heart and is measured by at least one electrode pair in contact with the user's skin;
monitoring a phase component of the heart activity measurement signal by computing an argument of wavelet-transformed in-phase (I) and quadrature (Q) components of the heart activity measurement signal;
computing at least one of a deviation, variance and variability of the phase of the QRS complex waveforms within a determined window;
detecting that at least one of the deviation, variance and variability exceeds a predetermined threshold; and
outputting, in response to said detecting, an instruction for the user to adjust at least one electrode of the at least one electrode pair.

7. The method of claim 6, wherein said action comprises determining a physiological parameter of the user from the phases of the QRS complex waveforms of the heart activity measurement signal.

8. The method of claim 7, wherein said determining the physiological parameter comprises:
determining a periodicity of the phase component of the heart activity measurement signal within the determined window; and
determining a respiratory rate of the user from the periodicity of the phase component of the heart activity measurement signal within the determined window.

9. The method of claim 6, wherein said action comprises:
determining interference signal components in the acquired heart activity measurement signal on the basis of the phase of the QRS complex waveform of the heart activity measurement signal; and
eliminating the determined interference signal components from further analysis of the heart activity measurement signal.

10. A computer program product embodied on a non-transitory distribution medium readable by a computer and comprising program instructions which, when executed, perform operations comprising:
acquiring a heart activity measurement signal of a user during a physical exercise performed by the user, wherein the heart activity measurement signal comprises QRS complex waveforms and characterizes electric activity of the user's heart and is measured by at least one electrode pair in contact with the user's skin;

monitoring a phase component of the heart activity measurement signal by computing an argument of wavelet-transformed in-phase (I) and quadrature (Q) components of the heart activity measurement signal;
computing at least one of a deviation, variance and variability of the phase of the QRS complex waveforms within a determined window;
detecting that at least one of the deviation, variance and variability exceeds a predetermined threshold; and
outputting, in response to said detecting, an instruction for the user to adjust at least one electrode of the at least one electrode pair.

11. A method for processing a heart activity measurement signal, the method comprising:
acquiring a first heart activity measurement signal of a user during a physical exercise performed by the user, wherein the first heart activity measurement signal comprises a first QRS complex waveform and characterizes electric activity of the user's heart and is measured by a first measurement configuration using at least one electrode pair in contact with the user's skin;
acquiring at least a second heart activity measurement signal of the user during the physical exercise, wherein the second heart activity measurement signal comprises a second QRS complex waveform and is measured by a second measurement configuration using at least one electrode pair not used for measuring the first heart activity measurement signal;
monitoring a phase component of the first heart activity measurement signal by computing an argument of wavelet-transformed in-phase (I) and quadrature (Q) components of the first heart activity measurement signal;
monitoring a phase component of the second heart activity measurement signal by computing an argument of wavelet-transformed in-phase (I) and quadrature (Q) components of the second heart activity measurement signal;
determining which one of the first and second QRS complex waveforms is within a predetermined range; and
selecting one of the first and second measurement configurations for use based on which one of the first and second measurement configurations provides the QRS complex waveform within the predetermined range.

12. An apparatus, the apparatus comprising:
at least one processor; and
at least one memory including a computer program code, wherein the at least one memory and the computer program code are configured, with the at least one processor, to cause the apparatus to perform operations comprising:
acquiring a first heart activity measurement signal of a user during a physical exercise performed by the user, wherein the first heart activity measurement signal comprises a first QRS complex waveform and characterizes electric activity of the user's heart and is measured by a first measurement configuration using at least one electrode pair in contact with the user's skin;
acquiring at least a second heart activity measurement signal of the user during the physical exercise, wherein the second heart activity measurement signal comprises a second QRS complex waveform and is measured by a second measurement configuration using at least one electrode pair not used for measuring the first heart activity measurement signal;
monitoring a phase component of the first heart activity measurement signal by computing an argument of wavelet-transformed in-phase (I) and quadrature (Q) components of the first heart activity measurement signal;
monitoring a phase component of the second heart activity measurement signal by computing an argument of wavelet-transformed in-phase (I) and quadrature (Q) components of the second heart activity measurement signal;
determining which one of the first and second QRS complex waveforms is within a predetermined range; and
selecting one of the first and second measurement configurations for use based on which one of the first and second measurement configurations provides the QRS complex waveform within the predetermined range.

* * * * *